United States Patent [19]

Ingersoll et al.

[11] 4,201,577
[45] May 6, 1980

[54] CERAMIC SUBSTRATE ALLOY

[75] Inventors: Clyde E. Ingersoll, Tonawanda; Dwarika P. Agarwall, Williamsville, both of N.Y.

[73] Assignee: Williams Gold Refining Company Incorporated, Buffalo, N.Y.

[21] Appl. No.: 958,563

[22] Filed: Nov. 8, 1978

[51] Int. Cl.² .................................................. C22C 5/02
[52] U.S. Cl. .................................. 75/134 N; 75/165; 75/172 G
[58] Field of Search ................. 75/134 N, 165, 172 G

[56] References Cited

U.S. PATENT DOCUMENTS

| 2,143,217 | 1/1939 | Truthe | 75/135 |
|---|---|---|---|
| 3,374,123 | 3/1968 | Masumoto et al. | 75/172 G |
| 3,667,936 | 6/1972 | Katz | 75/165 |
| 3,716,356 | 2/1973 | Burnett | 75/165 |
| 3,981,723 | 9/1976 | Tuccillo | 75/165 |
| 4,123,262 | 10/1978 | Cascone | 75/165 |

OTHER PUBLICATIONS

Nielsen et al. *Journal of Dental Research*, vol. 45, No. 3, Part 2, pp. 964–969, May–Jun., 1966.

Primary Examiner—L. Dewayne Rutledge
Assistant Examiner—Peter K. Skiff
Attorney, Agent, or Firm—Christel, Bean & Linihan

[57] ABSTRACT

An alloy composition enabling the amount of silver therein to be limited significantly or preferably eliminated altogether while maintaining the castability, strength properties and physical properties including melting range and coefficient of thermal expansion compatible with available porcelain products. The alloy composition contains, by weight, silver 0–11.0%, aluminum 0–1%, gold 31.8–63.16%, boron 0–0.13%, calcium 0–0.12%, copper 0–5.0%, iron 0–0.75%, gallium 0–5.0%, indium 0.5–10.55%, lithium 0–0.04%, nickel 0–2%, palladium 28.96–57.97%, rhenium 0–0.25%, ruthenium 0–1.8%, silicon 0–0.0125%, tin 0–7.5%, titanium 0–0.06%, vanadium 0–0.12% and zinc 0–1.98%.

7 Claims, No Drawings

CERAMIC SUBSTRATE ALLOY

BACKGROUND OF THE INVENTION

This invention relates to the art of alloys for dental purposes and the like, and more particularly to a new and improved alloy for use with porcelain for dental restorations.

There have been several generations of alloys for use with porcelain for dental restorations, and the first successful alloy system, known as yellow alloy, had a relatively high gold content, i.e. about 85 percent by weight, with platinum and palladium being the primary additions. The second generation alloy, known as white alloy, included a greater proportion by weight of platinum to provide greater strength. Eventually, cost reduction became an important consideration, and as a result both the yellow and white alloys were diluted with silver and the high priced platinum was removed. Then gold was removed to provide the final cost reduction.

The addition of silver, however, gave rise to an unexpected and undesirable result. Dental castings frequently are preoxidized in a temperature range of 1700° F. to 1950° F. prior to application of porcelain on the metal with the resulting oxide acting as a bonding agent between the metal and porcelain. Also, it is common to put a gold layer on the metal, before porcelainizing, by painting a gold powder slurry on the metal and then melting the gold in place at a temperature of about 1945° F. The porcelain then is fired to the surface of the metal in several "bakes" up to a temperature of about 1750° F.-1850° F. Thus, the cast substrate is in the furnace several times at temperatures ranging from about 1200° F. to about 1950° F.

Silver has a vapor pressure of about 1 μm at 1700° F. and about 10 μm at about 1950° F. and consequently some silver can vaporize during firing operations if the concentration in the alloy is sufficiently high. The resulting silver vapor then may condense in a very finely divided state on the surface of the porcelain being fired. If another layer of porcelain is fired over this condensed silver, the silver acts as a pigment and changes the shade of the porcelain. The most noticeable change is the grey of the silver interacting with the yellow tint of the porcelain to produce a greenish hue which is very undesirable.

SUMMARY OF THE INVENTION

It is, therefore, a primary object of this invention to provide a new and improved alloy for dental purposes and the like.

It is a more particular object of this invention to provide a new and improved alloy for use with porcelain for dental restorations.

It is a more particular object of this invention to provide a dental alloy wherein the amount of silver is significantly limited or preferably eliminated altogether while the alloy still maintains castability, strength properties, and physical properties including melting range and coefficient of thermal expansion compatible with available porcelain products.

The present invention provides an alloy for use with porcelain for dental restorations incorporating the following ranges of constituents in percentages by weight:

| Constituents | Proportional Range |
| --- | --- |
| Silver | 0–11.0 |
| Aluminum | 0–1 |
| Gold | 31.8–63.16 |
| Boron | 0–0.13 |
| Calcium | 0–0.12 |
| Copper | 0–5.0 |
| Iron | 0–0.75 |
| Gallium | 0–5.0 |
| Indium | 0.5–10.55 |
| Lithium | 0–0.04 |
| Nickel | 0–2 |
| Palladium | 28.96–57.97 |
| Rhenium | 0–0.25 |
| Ruthenium | 0–1.8 |
| Silicon | 0–0.0125 |
| Tin | 0–7.5 |
| Titanium | 0–0.06 |
| Vanadium | 0–0.12 |
| Zinc | 0–1.98 |

The alloy of the present invention possesses castability, strength properties, and physical properties including melting range and coefficient of thermal expansion compatible with available porcelain products.

DETAILED DESCRIPTION OF THE INVENTION

The relative proportions of the various elements comprising the alloy composition of the present invention enable the amount of silver in the alloy to be limited significantly or preferably eliminated altogether while maintaining the castability, strength properties, and physical properties including melting range and coefficient of thermal expansion compatible with available porcelain products. In particular, the alloy composition of the present invention contains by weight, silver 0–11%, aluminum 0–1%, gold 31.8–63.16%, boron 0–0.13%, calcium 0–0.12%, copper 0–5.0%, iron 0–0.75%, gallium 0–5.0%, indium 0.5–10.55%, lithium 0–0.04%, nickel 0–2%, palladium 28.96–57.97%, rhenium 0–0.25%, ruthenium 0–1.8%, silicon 0–0.0125%, tin 0–7.5%, titanium 0–0.06%, vanadium 0–0.12%, and zinc 0–1.98%. Preferred alloy compositions are those which contain, by weight, silver 0–5.86%, aluminum 0–0.3%, gold 40–60%, boron 0–0.13%, calcium 0–0.12%, copper 0–3%, iron 0–0.5%, gallium 0–1.8%, indium 2.5–10.55%, lithium 0–0.04%, nickel 0–2%, palladium 35–55%, rhenium 0–0.25%, ruthenium 0–0.6%, silicon 0–0.0125%, tin 0.5–4%, titanium 0–0.06%, vanadium 0–0.03%, and zinc 0–1%, with the proviso that the total of rhenium and ruthenium is at least 0.05% and the total of gallium, indium and tin is at least 3.5%.

The role of the respective alloying elements is believed to be as follows. Gold, one of the elements present in a substantial proportion by weight, improves the corrosion and tarnish resistance of alloy and contributes to the color thereof. Palladium, another of the elements present in a substantial proportion by weight, improves the corrosion and tarnish resistance of the alloy and contributes to the hardness and strength of the alloy. The additive elements are of several categories, and those serving as deoxidizers or oxygen scavengers for removing unwanted oxygen and or oxides during the alloying and subsequent remelting procedures include aluminum, boron, calcium, indium, lithium, tin, silicon, titanium, vanadium and zinc.

Boron, rhenium, ruthenium, titanium and vanadium serve as grain refiners to produce and maintain grain size. It is preferable to maintain an average grain diameter of less than 50μ, because as the molten alloy solidifies, the last part to harden is at the grain to grain interface. With precious metal alloys, the larger the diameter of the grains or particles making up this interface the greater the likelihood of a weakness or fault developing in the finished casting. It is therefore advantageous to add components to the alloy composition which will cause the formation of smaller grains at this interface. The smaller grains distribute the interface over a greater area thereby reducing the formation of potential weakspots. Rhenium and ruthenium in particular, are known to be useful in reducing or maintaining grain size diameter. It is preferred that both rhenium and ruthenium are present in the alloy composition to insure a sufficiently small grain size. Increasing the total amount of rhenium and ruthenium in a given alloy composition from 0.05% of each to 0.175% of each will cause the grain size diameter to decrease from about 30μ to about 14μ.

Those additive elements serving as surface oxide producers for bonding porcelain include aluminum, boron, copper, iron, gallium, indium, nickel, tin, titanium, and vanadium. Aluminum and gallium function to control surface oxide to limit the excessive growth of oxides.

Several of the additive elements serve to increase the coefficient of thermal expansion of the alloy. Pure gold has a coefficient of thermal expansion of $14.16 \times 10^{-6}$ and pure palladium has a coefficient of $11.76 \times 10^{-6}$. Alloys of these two metals alone theoretically would have a coefficient of thermal expansion between these two values. The thermal expansion coefficient must be greater than this intermediate value, however, to render the alloy compatible with popular porcelains. Additive elements having a higher coefficient to increase the coefficient of the resulting alloy include:

| Additive Element | Coefficient of Thermal Expansion |
| --- | --- |
| Silver | $19.68 \times 10^{-6}$ |
| Aluminum | $23.6 \times 10^{-6}$ |
| Calcium | $22.3 \times 10^{-6}$ |
| Copper | $16.6 \times 10^{-6}$ |
| Gallium | $18.0 \times 10^{-6}$ |
| Indium | $33.0 \times 10^{-6}$ |
| Nickel | $13.3 \times 10^{-6}$ |
| Tin | $19.9 \times 10^{-6}$ |
| Zinc | $39.7 \times 10^{-6}$ |

Some of the additive elements provide melting temperature control. Since porcelain is fired on the cast metal at about 1800° F., and pure gold frequently is melted on the surface at about 1950° F., the melting range of the alloy must be sufficiently above these two temperatures to avoid deformation when it is heated to these temperatures. Elements which tend to raise the melting range to acceptable levels include palladium, rhenium, ruthenium, titanium and vanadium.

The resulting alloy must resist discoloration or tarnish and corrosion in the mouth, and the additive elements which assist in tarnish and corrosion resistance include gold, indium, palladium, ruthenium, tin and titanium. Since the gold-palladium combination is inherently a weak alloy and no combination of the two would yield an alloy having sufficient yield strength to withstand masticatory forces, elements are added to increase the strength including aluminum, boron, calcium, copper, iron, gallium, indium, nickel, palladium, rhenium, ruthenium, tin, vanadium and zinc. Certain elements improve the ability of the molten alloy to fill an intricate mold by increasing the fluidity or by decreasing the surface tension of the melt, and those added to improve castability include silver, copper, indium and tin. Dilution elements of lower cost which may or may not affect other properties include silver, copper, gallium, indium, nickel, tin, titanium, vanadium, and zinc. Also while certain elements are included in several of the foregoing categories, their use may be governed by their effect on other requirements. For example, boron is beneficial as oxygen scavenger, grain refiner, surface oxide producer and strengthener, but its lowering the coefficient of thermal expansion, i.e. the coefficient for boron is $8.3 \times 10^{-6}$, and its strong lowering of the melting temperature in combination with palladium limits its use to only a trace amount.

The alloy of the present invention is made according to standard induction melting procedures and is rolled into flat pieces or elements with annealing at stages of the rolling operations.

The alloy of the present invention is illustrated further by Examples I–XXXV presented herein. Hardness data is given for each example and is taken with a standard diamond pyramid indenter under a one kilogram load. Since hardness is not translatable from one alloy system to another, some other mechanical property must be employed to compare different systems. In the present case, the 0.2% offset yield strength was used as the comparable property. The Vickers hardness shown in the examples is for a cast alloy of this invention, after the porcelain application heat cycle, having the same yield strength characteristics as alloys which come under the American Dental Association Specification 5 for dental castings. For a more detailed description of the Specification, reference may be made to U.S. Pat. Nos. 3,929,474 issued Dec. 30, 1975 and 3,929,475 issued Dec. 30, 1975 both assigned to the assignee of the present invention, the disclosures of both of which are hereby incorporated by reference. The alloy of the present invention, as illustrated in Examples I–XXXV, has a Vickers hardness which is within the range called for by ADA Specification 5.

The melting temperature range in degrees Fahrenheit is given for each example. The melting temperature range is obtained by a standard cooling curve method wherein the upper limit of the melting range (liquidus) and the lower limit thereof (solidus) are obtained by noting the changes of the slope in the temperature vs. time curve obtained by the use of a Pt-Pt 13Rh thermocouple in the melt. The solidus temperature in each instance is sufficiently above the temperature of about 1800° F. at which porcelain is fired on the cast metal so as to avoid deformation. Generally speaking a margin of about 100° F. is desirable. Also, with the possible exception of Example XXI, the solidus temperature in each instance is sufficiently above the temperature of about 1950° F. at which pure gold in some situations is melted on the surface of the cast metal. In addition, it is desirable that the solidus temperature be above the soldering or brazing temperature range of 2000° F.–2100° F. encountered in dental work, and this is the case for many of the examples herein.

The coefficient of thermal expansion (C.T.E.) of the alloy is calculated according to known procedures for each of the examples. In addition, for some of the examples, the coefficient of thermal expansion (C.T.E.) of the alloy is measured by the use of an Orton dilatometer. In each instance, the coefficient of the alloy according to the present invention has a value making the alloy compatible with popular porcelains.

The yield strength was measured for the alloys of Examples XXV and XXVI by standard methods. For the remaining examples however, hardness is used as an indicator since it involves a test which consumes less time and effort as compared to yield strength testing and since in the same alloy system yield strength is proportional to hardness. Tests on tarnishability were conducted on the alloys of Examples XXV–XXXIV according to the method described in either of the above-referenced U.S. Pat. Nos. 3,929,474 and 3,929,475. Briefly a numerical scale beginning at zero for nonexposure was established using ammonium sulfide vapors. The alloys of Examples XXV and XXVII when tested indicated no tarnish or change in color when exposed to the sulfide vapor. Examples XXVII–XXXIV when tested indicated a minor change in color when exposed to the sulfide vapor (i.e. reading ranged from ½ to 1). In addition, the alloy of the present invention was observed to have sufficient fluidity in the molten state or condition to fill an intricate mold thereby possessing the degree of castability required for dental alloys and the like.

The alloy of the present invention is illustrated further by the following examples.

EXAMPLE I

| Constituent | Composition In Weight % |
|---|---|
| Silver | 1.17 |
| Gold | 63.16 |
| Indium | 1.75 |
| palladium | 30.99 |
| Tin | 2.92 |
| Vickers Hardness | 108 |
| Melting Range, °F. | 2340–2490 |
| C.T.E. calculated | $13.98 \times 10^{-6}$ |

EXAMPLE II

| Constituent | Composition In Weight % |
|---|---|
| Silver | 5.0 |
| Gold | 31.8 |
| Boron | .05 |
| Copper | 1.0 |
| Indium | 1.5 |
| Palladium | 57.97 |
| Ruthenium | 0.18 |
| Tin | 2.5 |
| Vickers Hardness | 131 |
| Melting Range, °F. | 2570–2630 |
| C.T.E. calculated | $13.50 \times 10^{-6}$ |
| C.T.E. measured | $13.5 \times 10^{-6}$ |

EXAMPLE III

| Constituent | Composition In Weight % |
|---|---|
| Gold | 50.0 |
| Boron | 0.08 |

-continued

| Constituent | Composition In Weight % |
|---|---|
| Copper | 3.0 |
| Indium | 1.5 |
| Palladium | 42.74 |
| Ruthenium | 0.18 |
| Tin | 2.5 |
| Vickers Hardness | 154 |
| Melting Range, °F. | 2375–2520 |
| C.T.E. calculated | $13.63 \times 10^{-6}$ |

EXAMPLE IV

| Constituent | Composition In Weight % |
|---|---|
| Silver | 7.65 |
| Gold | 59.02 |
| Indium | 1.64 |
| Palladium | 28.96 |
| Tin | 2.73 |
| Vickers Hardness | 113 |
| Melting Range, °F. | 2310–2415 |
| C.T.E. calculated | $14.36 \times 10^{-6}$ |

EXAMPLE V

| Constituent | Composition In Weight % |
|---|---|
| Gold | 48.5 |
| Boron | 0.08 |
| Calcium | 0.07 |
| Gallium | 1.5 |
| Indium | 6.93 |
| Palladium | 40.87 |
| Ruthenium | 1.0 |
| Tin | 1.0 |
| Titanium | 0.05 |
| Vickers Hardness | 223 |
| Melting Range, °F. | 2290–2390 |
| C.T.E. calculated | $14.64 \times 10^{-6}$ |

EXAMPLE VI

| Constituent | Composition In Weight % |
|---|---|
| Gold | 49.0 |
| Boron | 0.08 |
| Calcium | 0.07 |
| Indium | 5.43 |
| Palladium | 41.32 |
| Rhenium | 0.05 |
| Ruthenium | 0.05 |
| Tin | 4.0 |
| Vickers Hardness | 177 |
| Melting Range °F. | 2280–2440 |
| C.T.E. calculated | $14.43 \times 10^{-6}$ |
| C.T.E. measured | $13.7 \times 10^{-6}$ |

EXAMPLE VII

| Constituent | Composition In Weight % |
|---|---|
| Aluminum | 1.0 |
| Gold | 49.0 |

| Constituent | Composition In Weight % |
|---|---|
| Boron | 0.08 |
| Calcium | 0.12 |
| Copper | 3.66 |
| Iron | 0.5 |
| Indium | 2.5 |
| Nickel | 1.0 |
| Palladium | 37.73 |
| Ruthenium | 0.6 |
| Tin | 2.5 |
| Titanium | 0.06 |
| Vanadium | 0.03 |
| Zinc | 1.22 |
| Vickers Hardness | 319 |
| Melting Range, °F. | 2005–2100 |
| C.T.E. calculated | 14.32 × 10⁻⁶ |

EXAMPLE VIII

| Constituent | Composition In Weight % |
|---|---|
| Aluminum | 0.5 |
| Gold | 49.5 |
| Boron | 0.08 |
| Calcium | 0.12 |
| Copper | 3.66 |
| Iron | 0.5 |
| Indium | 2.5 |
| Nickel | 1.5 |
| Palladium | 36.63 |
| Ruthenium | 0.7 |
| Tin | 2.5 |
| Titanium | 0.06 |
| Vanadium | 0.03 |
| Zinc | 1.22 |
| Vickers Hardness | 306 |
| Melting Range, °F. | 2065–2175 |
| C.T.E. calculated | 14.22 × 10⁻⁶ |

EXAMPLE IX

| Constituent | Composition In Weight % |
|---|---|
| Aluminum | 0.3 |
| Gold | 50.0 |
| Boron | 0.08 |
| Calcium | 0.12 |
| Copper | 3.66 |
| Indium | 2.2 |
| Nickel | 1.0 |
| Palladium | 38.23 |
| Ruthenium | 0.6 |
| Tin | 2.5 |
| Titanium | 0.06 |
| Vanadium | 0.03 |
| Zinc | 1.22 |
| Vickers Hardness | 209 |
| Melting Range, °F. | 2145–2280 |
| C.T.E. calculated | 14.19 × 10⁻⁶ |

EXAMPLE X

| Constituent | Composition In Weight % |
|---|---|
| Aluminum | 0.1 |
| Gold | 50.0 |
| Boron | 0.08 |
| Calcium | 0.12 |
| Copper | 3.66 |
| Indium | 2.5 |
| Nickel | 1.0 |
| Palladium | 37.93 |
| Ruthenium | 0.8 |
| Tin | 2.5 |
| Titanium | 0.06 |
| Vanadium | 0.03 |
| Zinc | 1.22 |
| Vickers Hardness | 185 |
| Melting Range, °F. | 2175–2310 |
| C.T.E. calculated | 14.22 × 10⁻⁶ |

EXAMPLE XI

| Constituent | Composition In Weight % |
|---|---|
| Silver | 5.0 |
| Gold | 51.4 |
| Boron | 0.08 |
| Copper | 2.0 |
| Indium | 1.5 |
| Palladium | 37.25 |
| Ruthenium | 0.18 |
| Tin | 2.5 |
| Vickers Hardware | 145 |
| Melting Range, °F. | 2380–2470 |
| C.T.E. calculated | 14.00 × 10⁻⁶ |

EXAMPLE XII

| Constituent | Composition In Weight % |
|---|---|
| Gold | 49.5 |
| Boron | 0.08 |
| Calcium | 0.12 |
| Copper | 3.66 |
| Iron | 0.75 |
| Indium | 2.0 |
| Nickel | 1.0 |
| Palladium | 38.12 |
| Ruthenium | 0.5 |
| Tin | 3.0 |
| Titanium | 0.05 |
| Zinc | 1.22 |
| Vicker Hardness | 197 |
| Melting Range, °F. | 2080–2140 |
| C.T.E. calculated | 14.15 × 10⁻⁶ |
| C.T.E. measured | 14.2 × 10⁻⁶ |

EXAMPLE XIII

| Constituent | Composition In Weight % |
|---|---|
| Gold | 48.5 |
| Boron | 0.08 |
| Calcium | 0.07 |
| Gallium | 0.5 |
| Indium | 6.93 |
| Palladium | 40.70 |
| Ruthenium | 0.175 |
| Tin | 3.0 |
| Titanium | 0.04 |
| Vickers Hardness | 246 |

-continued

| Constituent | Composition In Weight % |
|---|---|
| Melting Range, °F. | 2190–2380 |
| C.T.E. calculated | 14.68 × 10$^{-6}$ |

EXAMPLE XIV

| Constituent | Composition In Weight % |
|---|---|
| Gold | 50.0 |
| Boron | 0.08 |
| Calcium | 0.12 |
| Copper | 3.66 |
| Gallium | 1.0 |
| Indium | 2.5 |
| Nickel | 1.0 |
| Palladium | 37.03 |
| Ruthenium | 0.8 |
| Tin | 2.5 |
| Titanium | 0.06 |
| Vanadium | 0.03 |
| Zinc | 1.22 |
| Vickers Hardness | 284 |
| Melting Range, °F. | 2140–2230 |
| C.T.E. calculated | 14.31 × 10$^{-6}$ |

EXAMPLE XV

| Constituent | Composition In Weight % |
|---|---|
| Gold | 49.5 |
| Boron | 0.08 |
| Calcium | 0.10 |
| Copper | 2.93 |
| Gallium | 0.8 |
| Indium | 3.0 |
| Palladium | 38.76 |
| Ruthenium | 0.80 |
| Tin | 2.0 |
| Titanium | 0.06 |
| Zinc | 1.98 |
| Vickers Hardness | 219 |
| Melting Range, °F. | 2080–2140 |
| C.T.E. calculated | 14.47 × 10$^{-6}$ |

EXAMPLE XVI

| Constituent | Composition In Weight % |
|---|---|
| Gold | 48.5 |
| Boron | 0.08 |
| Calcium | 0.10 |
| Copper | 2.93 |
| Gallium | 0.8 |
| Indium | 4.0 |
| Palladium | 40.47 |
| Ruthenium | 1.1 |
| Tin | 1.0 |
| Titanium | 0.05 |
| Zinc | 0.98 |
| Vickers Hardness | 184 |
| Melting Range, °F. | 2180–2220 |
| C.T.E. calculated | 14.29 × 10$^{-6}$ |

EXAMPLE XVII

| Constituent | Composition In Weight % |
|---|---|
| Gold | 48.5 |
| Boron | 0.08 |
| Calcium | 0.10 |
| Copper | 1.94 |
| Gallium | 1.1 |
| Indium | 5.5 |
| Palladium | 40.85 |
| Ruthenium | 1.32 |
| Tin | 1.0 |
| Titanium | 0.05 |
| Zinc | 0.97 |
| Vickers Hardness | 252 |
| Melting Range, °F. | 2050–2400 |
| C.T.E. calculated | 14.63 × 10$^{-6}$ |

EXAMPLE XVIII

| Constituent | Composition In Weight % |
|---|---|
| Gold | 50.0 |
| Boron | 0.08 |
| Calcium | 0.12 |
| Copper | 3.66 |
| Iron | 0.5 |
| Indium | 2.5 |
| Nickel | 2.0 |
| Palladium | 36.73 |
| Ruthenium | 0.6 |
| Tin | 2.5 |
| Titanium | 0.06 |
| Vanadium | 0.03 |
| Zinc | 1.22 |
| Vickers Hardness | 203 |
| Melting Range, °F. | 2125–2260 |
| C.T.E. calculated | 14.25 × 10$^{-6}$ |
| C.T.E. measured | 14.5 × 10$^{-6}$ |

EXAMPLE XIX

| Constituent | Composition In Weight % |
|---|---|
| Gold | 50.0 |
| Boron | 0.08 |
| Copper | 3.0 |
| Indium | 2.0 |
| Nickel | 1.0 |
| Palladium | 40.07 |
| Ruthenium | 0.35 |
| Tin | 2.5 |
| Zinc | 1.0 |
| Vickers Hardness | 179 |
| Melting Range, °F. | 2250–2405 |
| C.T.E. calculated | 14.03 × 10$^{-6}$ |

EXAMPLE XX

| Constituent | Composition In Weight % |
|---|---|
| Gold | 50.0 |
| Boron | 0.08 |
| Calcium | 0.1 |
| Copper | 3.0 |
| Indium | 2.0 |
| Nickel | 1.0 |

| Constituent | Composition In Weight % |
|---|---|
| Palladium | 39.77 |
| Ruthenium | 1.5 |
| Tin | 2.5 |
| Titanium | 0.05 |
| Zinc | 1.0 |
| Vickers Hardness | 175 |
| Melting Range, °F. | 2240–2390 |
| C.T.E. calculated | $14.02 \times 10^{-6}$ |

EXAMPLE XXI

| Constituent | Composition In Weight % |
|---|---|
| Gold | 49.0 |
| Boron | 0.08 |
| Calcium | 0.07 |
| Gallium | 1.0 |
| Indium | 6.43 |
| Palladium | 40.97 |
| Ruthenium | 1.8 |
| Tin | 1.0 |
| Titanium | 0.05 |
| Vickers Hardness | 199 |
| Melting Range, °F. | 1960–2500 |
| C.T.E. calculated | $14.41 \times 10^{-6}$ |

EXAMPLE XXII

| Constituent | Composition In Weight % |
|---|---|
| Gold | 48.5 |
| Boron | 0.08 |
| Calcium | 0.07 |
| Indium | 6.93 |
| Palladium | 40.82 |
| Rhenium | 0.05 |
| Ruthenium | 0.05 |
| Tin | 3.5 |
| Vickers Hardness | 221 |
| Melting Range, °F. | 2170–2350 |
| C.T.E. calculated | $14.70 \times 10^{-6}$ |
| C.T.E. measured | $14.0 \times 10^{-6}$ |

EXAMPLE XXIII

| Constituent | Composition In Weight % |
|---|---|
| Gold | 50.0 |
| Boron | 0.08 |
| Calcium | 0.12 |
| Copper | 3.66 |
| Iron | 0.5 |
| Indium | 2.5 |
| Nickel | 1.0 |
| Palladium | 37.75 |
| Ruthenium | 0.6 |
| Tin | 2.5 |
| Titanium | .06 |
| Vanadium | 0.01 |
| Vickers Hardness | 203 |
| Melting Range, °F. | 2100–2320 |
| C.T.E. calculated | $14.23 \times 10^{-6}$ |

EXAMPLE XXIV

| Constituent | Composition In Weight % |
|---|---|
| Gold | 50.0 |
| Boron | .08 |
| Calcium | 0.12 |
| Copper | 3.66 |
| Iron | 0.5 |
| Indium | 2.5 |
| Nickel | 1.0 |
| Palladium | 37.74 |
| Ruthenium | 0.6 |
| Tin | 2.5 |
| Titanium | 0.06 |
| Vanadium | 0.02 |
| Vickers Hardness | 198 |
| Melting Range, °F. | 2265–2300 |
| C.T.E. calculated | $14.23 \times 10^{-6}$ |

EXAMPLE XXV

| Constituent | Composition In Weight % |
|---|---|
| Gold | 48.50 |
| Boron | 0.13 |
| Calcium | 0.08 |
| Indium | 6.92 |
| Palladium | 41.77 |
| Rhenium | 0.05 |
| Ruthenium | 0.05 |
| Tin | 3.50 |
| Vickers Hardness | 219 |
| Melting Range, °F. | 2095–2235 |
| C.T.E. calculated | $14.58 \times 10^{-6}$ |
| C.T.E. measured | $13.8 \times 10^{-6}$ |
| 0.2% Offset Yield Strength, psi | 79,000 |
| Tarnish | 0 |

EXAMPLE XXVI

| Constituent | Composition In Weight % |
|---|---|
| Aluminium | 0.01 |
| Gold | 48.46 |
| Boron | 0.02 |
| Calcium | 0.08 |
| Indium | 9.92 |
| Lithium | 0.04 |
| Palladium | 39.91 |
| Rhenium | 0.03 |
| Ruthenium | 0.03 |
| Silicon | 0.01 |
| Tin | 1.50 |
| Vickers Hardness | 215 |
| Melting Range, °F. | 2260–2415 |
| C.T.E. calculated | $15.10 \times 10^{-6}$ |
| C.T.E. measured | $13.8 \times 10^{-6}$ |
| 0.2% Offset Yield Strength, psi | 75,200 |
| Tarnish | 0 |

EXAMPLE XXVII

| Constituent | Composition In Weight % |
|---|---|
| Gold | 48.725 |
| Boron | 0.02 |
| Gallium | 0.50 |

-continued

| Constituent | Composition In Weight % |
|---|---|
| Indium | 10.55 |
| Lithium | 0.025 |
| Palladium | 39.63 |
| Rhenium | 0.025 |
| Ruthenium | 0.025 |
| Tin | 0.5 |
| Vickers Hardness | 224 |
| Melting Range, °F. | 2255–2375 |
| 0.2% Offset Yield Strength psi | 71,700 |
| C.T.E. Calculated | $15.24 \times 10^{-6}$ |
| C.T.E. Measured | $14.02 \times 10^{-6}$ |
| Tarnish | 0 |

EXAMPLE XXVIII

| Constituent | Composition In Weight % |
|---|---|
| Silver | 11.0 |
| Gold | 43.0 |
| Boron | 0.075 |
| Calcium | 0.075 |
| Copper | 1.0 |
| Gallium | 1.0 |
| Indium | 1.925 |
| Nickel | 0.5 |
| Palladium | 35.575 |
| Rhenium | 0.175 |
| Ruthenium | 0.175 |
| Tin | 5.5 |
| Vickers Hardness | 276 |
| Melting Range, °F. | 2090–2155 |
| 0.2% Offset Yield Strength, psi | 91,900 |
| C.T.E. Calculated | $14.63 \times 10^{-6}$ |
| C.T.E. Measured | $14.97 \times 10^{-6}$ |
| Tarnish | ½ |

EXAMPLE XXIX

| Constituent | Composition In Weight % |
|---|---|
| Silver | 5.0 |
| Gold | 45.0 |
| Boron | 0.075 |
| Calcium | 0.075 |
| Copper | 5.0 |
| Indium | 1.925 |
| Nickel | 1 |
| Palladium | 40.075 |
| Rhenium | 0.175 |
| Ruthenium | 0.175 |
| Tin | 1.5 |
| Vickers Hardness | 172 |
| Melting Range, °F. | 2080–2280 |
| 0.2% Offset Yield Strength | 59,800 |
| C.T.E. Calculated | $14.01 \times 10^{-6}$ |
| C.T.E. Measured | $14.95 \times 10^{-6}$ |
| Tarnish | ½ |

EXAMPLE XXX

| Constituent | Composition In Weight % |
|---|---|
| Silver | 5.76 |
| Aluminum | 0.0125 |
| Gold | 45.0 |
| Boron | 0.025 |
| Copper | 4.0 |
| Gallium | 1.0 |
| Indium | 2.0 |
| Lithium | 0.04 |
| Nickel | 1.0 |
| Palladium | 39.15 |
| Rhenium | 0.25 |
| Ruthenium | 0.25 |
| Silicon | 0.0125 |
| Tin | 1.5 |
| Vickers Hardness | 182 |
| Melting Range, °F. | 2220–2380 |
| Yield Strength, psi | 39,500 |
| C.T.E. Calculated | $14.11 \times 10^{-6}$ |
| C.T.E. Measured | $14.20 \times 10^{-6}$ |
| Tarnish | ½ |

EXAMPLE XXXI

| Constituent | Composition In Weight % |
|---|---|
| Silver | 5.86 |
| Aluminum | 0.0125 |
| Gold | 44.8 |
| Boron | 0.025 |
| Gallium | 1.8 |
| Indium | 3.3 |
| Lithium | 0.04 |
| Nickel | 1.0 |
| Palladium | 40.45 |
| Rhenium | 0.25 |
| Ruthenium | 0.25 |
| Silicon | 0.0125 |
| Tin | 2.2 |
| Vickers Hardness | 205 |
| Melting Range, °F. | 2170–2340 |
| 0.2% Offset Yield Strength, psi | 78,400 |
| C.T.E. Calculated | $14.29 \times 10^{-6}$ |
| C.T.E. Measured | $14.62 \times 10^{-6}$ |
| Tarnish | 1 |

EXAMPLE XXXII

| Constituent | Composition In Weight % |
|---|---|
| Silver | 7.0 |
| Gold | 35.0 |
| Indium | 7.5 |
| Palladium | 50.4 |
| Rhenium | 0.1 |
| Vickers Hardness | 135 |
| Melting Range, °F. | 2460–2550 |
| 0.2% Offset Yield Strength psi | 22,200 |
| C.T.E. Calculated | $14.74 \times 10^{-6}$ |
| C.T.E. Measured | $13.78 \times 10^{-6}$ |
| Tarnish | ½ |

EXAMPLE XXXIII

| Constituent | Composition In Weight % |
|---|---|
| Silver | 3.0 |
| Gold | 40.0 |
| Indium | 5.0 |
| Palladium | 44.4 |
| Ruthenium | 0.1 |

-continued

| Constituent | Composition In Weight % |
| --- | --- |
| Tin | 7.5 |
| Vickers Hardness | 260 |
| Melting Range, °F. | 2135–2345 |
| 0.2% Offset yield Strength psi | 85,400 |
| C.T.E. Calculated | 14.63 × 10⁻⁶ |
| C.T.E. Measured | 14.18 × 10⁻⁶ |
| Tarnish | ½ |

EXAMPLE XXXIV

| Constituent | Composition In Weight % |
| --- | --- |
| Silver | 1.0 |
| Gold | 50 |
| Boron | 0.1 |
| Gallium | 5.0 |
| Indium | 0.5 |
| Palladium | 43.4 |
| Vickers Hardness | 320 |
| Melting Range, °F. | 2160–2260 |
| 0.2% Offset Yield Strength, psi | 105,200 |
| C.T.E. Calculated | 13.48 × 10⁻⁶ |
| C.T.E. Measured | 14.08 × 10⁻⁶ |
| Tarnish | ½ |

EXAMPLE XXXV

| Constituent | Composition In Weight % |
| --- | --- |
| Gold | 50.0 |
| Boron | .08 |
| Calcium | 0.12 |
| Copper | 3.66 |
| Iron | 0.5 |
| Indium | 2.5 |
| Nickel | 1.0 |
| Palladium | 37.45 |
| Ruthenium | 0.8 |
| Tin | 2.5 |
| Titanium | 0.06 |
| Vanadium | 0.12 |
| Zinc | 1.22 |
| Vickers Hardness | 207 |

*Other Test data (i.e. melting range and C.T.E.) etc were not determined for the Example.

When used in making dental restorations and the like, the alloy of the present invention is cast to the desired shape by standard casting procedures well-known in the art. The alloy is heated at the appropriate melting temperature until it pools and then cast using a standard dental casting machine. The alloy of the present invention has sufficient fluidity when melted for casting to fill an intricate mold completely.

After the casting of desired shape has been formed, the cast alloy of the present invention has at least one layer of porcelain applied thereto in the making of dental restorations. This is done according to standard procedures well known in the art, and frequently the dental castings are pre-oxidized at a temperature from about 1700° F. to about 1950° F. prior to applying porcelain on the metal with the resulting oxide acting as a bonding agent between the metal and porcelain. In addition, a gold layer commonly is applied to the metal, prior to porcelainizing, by painting a gold powder slurry on the metal and then melting the gold in place at a temperature of about 1945° F. Porcelain is applied to the casting by standard firing techniques well known in the art. This is done in at least one but typically several porcelain firing cycles or bakes at a temperature range of from about 1200° F. to about 1825° F. Commercially available porcelains can be used, for example one known as Will-Ceram Porcelain marketed by Williams Gold Refining Co. Inc. of Buffalo, New York.

The alloy of the present invention, characterized by the absence of silver or only a very insubstantial amount of silver, avoids the undesirable result of silver vaporization during the foregoing heating and firing operations. Advantageously, the alloy of the present invention enables the amount of silver therein to be limited significantly or preferably eliminated altogether while maintaining castability, strength properties and physical properties including melting range and coefficient of thermal expansion compatible with available porcelain products.

It is therefore apparent that the present invention accomplishes its intended objects. While the present invention has been described in detail, this is for the purpose of illustration, not limitation.

We claim:

1. An alloy suitable to have porcelain fired thereon consisting essentially of the following constituents in the indicated percentages by weight: silver 0–11.0%, aluminum 0–1.0%, gold 31.8–63.16%, boron 0–0.13%, calcium 0–0.12%, copper 0–5.0%, iron 0–0.75%, gallium 0–5.0%, indium 0.5–10.55%, lithium 0–0.04%, nickel 0–2.0%, palladium 28.96–57.97%, rhenium 0.025–0.25%, ruthenium 0.025–1.8%, silicon 0–0.0125%, tin 0–7.5%, titanium 0–0.06%, vanadium 0–0.12% and zinc 0–1.98%, with the proviso that both said rhenium and said ruthenium are present in the alloy composition, and the total of said rhenium and said ruthenium is at least 0.05% and the total of said gallium, indium and tin is at least 3.5%.

2. An alloy according to claim 1, consisting essentially of the following constituents in the indicated percentages by weight: silver 0–5.86%, aluminum 0–0.3%, gold 40.0–60.0%, boron 0–0.13%, calcium 0–0.12%, copper 0–3.0%, iron 0–0.5%, gallium 0–1.8%, indium 2.5–10.55%, lithium 0–0.04%, nickel 0–2.0%, palladium 35–55%, rhenium 0.025–0.25%, ruthenium 0.025–0.6%, silicon 0–0.0125%, tin 0.5–4.0%, titanium 0–0.06%, vanadium 0–0.03% and zinc 0–1.0%, with the proviso that both said rhenium and said ruthenium are present in the alloy composition, and the total of said rhenium and said ruthenium is at least 0.05% and the total of said gallium, indium and tin is at least 3.5%.

3. A cast alloy according to claim 1 provided with at least one layer of porcelain fired on the surface thereof.

4. An alloy suitable to have porcelain fired thereon consisting essentially of the following constituents in the indicated percentages by weight: silver 0–11.0%, aluminum 0–1.0%, gold about 48.5%, boron about 0.13%, calcium about 0.08%, copper 0–5.0%, iron 0–0.75%, gallium 0–5.0%, indium about 6.92%, lithium 0–0.04%, nickel 0–2.0%, palladium about 41.77%, rhenium about 0.05%, ruthenium about 0.05%, silicon 0–0.0125%, tin about 3.50%, titanium 0–0.06%, vanadium 0–0.12% and zinc 0–1.98%.

5. An alloy suitable to have porcelain fired thereon consisting essentially of the following constituents in the indicated percentages by weight: silver 0–11.0%, aluminum about 0.01%, gold about 48.46%, boron about 0.02%, calcium about 0.08%, copper 0–5.0%, iron 0–0.75%, gallium 0–5.0%, indium about 9.92%, lithium about 0.04%, nickel 0–2.0%, palladium about 39.91%, rhenium about 0.03%, ruthenium about 0.03%, silicon about 0.01%, tin about 1.50%, titanium 0–0.06%, vanadium 0–0.12% and zinc 0–1.98%.

6. An alloy suitable to have porcelain fired thereon consisting essentially of the following constituents in the indicated percentages by weight: silver 0–11.0%, aluminum 0–1.0%, gold about 48.725%, boron about 0.02%, calcium 0–0.12%, copper 0–5.0%, iron 0–0.75%, gallium about 0.50%, indium about 10.55%, lithium about 0.025%, nickel 0–2.0%, palladium about 39.63%, rhenium about 0.025%, ruthenium about 0.025%, silicon 0–0.0125%, tin about 0.5%, titanium 0–0.06%, vanadium 0–0.12% and zinc 0–1.98%.

7. An alloy suitable to have porcelain fired thereon consisting essentially of the following constituents in the indicated percentages by weight: silver 5.86%, aluminum 0.0125%, gold about 44.8%, boron about 0.025%, calcium 0–0.12%, copper 0–5.0, iron 0–0.75%, gallium about 1.8%, indium about 3.3%, lithium about 0.04%, nickel about 1.0%, palladium about 40.45%, rhenium about 0.25%, ruthenium about 0.25%, silicon about 0.0125%, tin about 2.2%, titanium 0–0.06%, vanadium 0–0.12% and zinc 0–1.98%.

* * * * *